United States Patent [19]

Schmitthaeusler et al.

[11] Patent Number: 5,700,426
[45] Date of Patent: Dec. 23, 1997

[54] METHOD FOR DECONTAMINATING OR STERILIZING "IN SITU" A VACUUM SEALED CONTAINER AND DEVICE FOR IMPLEMENTING SUCH METHOD

[75] Inventors: Roland Schmitthaeusler, Montigny-le-Bretonneux; Annie Bardat, Limours, both of France

[73] Assignee: Foundation Nationale de Transfusion Sanguine, Paris Cedex, France

[21] Appl. No.: 351,111

[22] Filed: Nov. 30, 1994

Related U.S. Application Data

[63] Continuation of Ser. No. 117,193, filed as PCT/FR92/00212, Mar. 9, 1992, published as WO92/15337, Sep. 17, 1992, abandoned.

[30] Foreign Application Priority Data

Mar. 8, 1991 [FR] France .................... 91 02812

[51] Int. Cl.⁶ .................................................. A61L 2/20
[52] U.S. Cl. ........................ 422/29; 422/33; 422/292
[58] Field of Search .................. 422/28, 29, 32, 422/33, 292

[56] References Cited

U.S. PATENT DOCUMENTS

| | | | |
|---|---|---|---|
| 3,615,727 | 10/1971 | Starke | 422/33 |
| 3,751,225 | 8/1973 | Karlson | 422/292 X |
| 3,900,288 | 8/1975 | Levine | 422/33 |
| 4,058,213 | 11/1977 | Stone | 422/41 X |
| 4,248,971 | 2/1981 | Youssef | 422/28 X |
| 4,687,518 | 8/1987 | Miyata et al. | 106/161 |
| 4,764,351 | 8/1988 | Hennenbert et al. | 422/33 X |
| 4,975,527 | 12/1990 | Koezuka et al. | 530/356 |
| 5,068,087 | 11/1991 | Childers | 422/26 |
| 5,286,448 | 2/1994 | Childers | 422/28 |
| 5,344,652 | 9/1994 | Hall, II et al. | 424/405 |
| 5,349,083 | 9/1994 | Brougham et al. | 562/6 |
| 5,413,758 | 5/1995 | Caputo et al. | 422/22 |

FOREIGN PATENT DOCUMENTS

| | | |
|---|---|---|
| 0261032 | 3/1988 | European Pat. Off. . |
| 0286506 | 10/1988 | European Pat. Off. . |
| 0369185 | 5/1990 | European Pat. Off. . |
| 3244465 | 10/1991 | Japan . |
| 8909068 | 10/1989 | WIPO . |

OTHER PUBLICATIONS

Kostenbauder, H.B., "Physical Factors influencing the activity of antimicrobial agents," pp. 811–813 of *Disinfection, Sterilization and Preservation* by Block, 1983.

Phillips, C.R., "Gaseous Sterilization," p. 682 of *Disinfection, Sterilization and Preservation* by Block, 1968.

*Primary Examiner*—Robert J. Warden
*Assistant Examiner*—Leigh Dawson
*Attorney, Agent, or Firm*—Foley & Lardner

[57] ABSTRACT

A method is described for decontaminating or sterilizing a vacuum sealed container, particularly after a lyophilization cycle, wherein one or a plurality of containers containing microorganisms or dangerous products by introducing an aqueous gas or liquid into the container after dehydration. Also described is a device for performing the method.

13 Claims, 1 Drawing Sheet

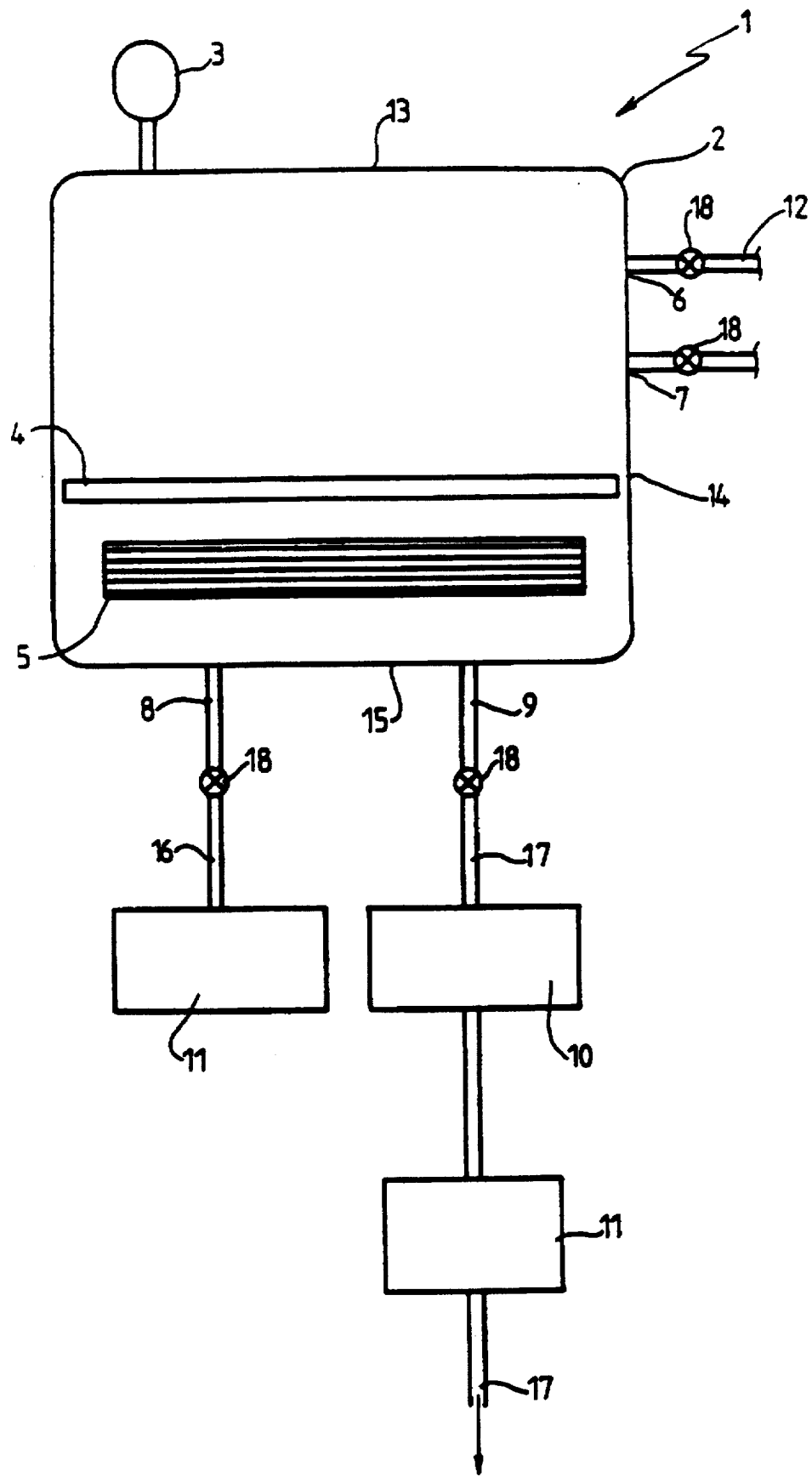

METHOD FOR DECONTAMINATING OR STERILIZING "IN SITU" A VACUUM SEALED CONTAINER AND DEVICE FOR IMPLEMENTING SUCH METHOD

This application is a continuation of application Ser. No. 08/117,193, filed as PCT/FR92/00212 Mar. 9, 1992 published as WO92/15337 Sep. 17, 1992, now abandoned.

The present invention relates to a method for decontaminating or sterilizing "in situ" a sealed container, especially after a vacuum-drying cycle for an active product, for example during a lyophilization. It also relates to a device for implementing the said method.

BACKGROUND OF THE INVENTION

Among the methods for preserving labile products, lyophilization (sublimation of ice under reduced pressure) currently constitutes the most reliable means for preserving the activity of a product during storage.

The pharmaceutical industry widely applies this technique to all active ingredients susceptible to undergoing a denaturation while the water content is too high. Lyophilization is all the more appropriate for pharmaceutical products since this technique is applied at the end of production, at the level of the final receptacle.

While the methods for preparing the lyophilizer are well codified, especially with respect to cleaning using the NEP methods and steam sterilization, the same does not apply to the discharging of the drying tank. Indeed, during sublimation, particles of active product may have been entrained by the flow of water vapor and occur in a random manner in the atmosphere of the tank. The operator responsible for collecting the manufactured product is thus exposed to contact with these aerosols, which may result in a high risk for his health: absorption of active ingredients in unknown doses via non-validated entry groups: respiratory tract, ocular region, skin exposure.

These dangerous situations are particularly frightening when the lyophilized product contains biological substances with replicative potential, such as bacteria, viruses, or isolated nucleic acids. This is the case for example for lyophilized vaccinal preparations or pathogenic strains of viruses or bacteria intended to the constitution of collections or alternatively for viral or bacterial vectors prepared for a veterinary or agricultural application (targeted parasitization of agents which are harmful for animals or plants).

There is also a risk during the lyophilization of products which may contain infectious viruses, such as for example HIV or HBV, potentially present in human blood and its derivatives, when the controls for viremia are not sufficiently sensitive or give false negatives or are not reliable.

Lyophilized medicinal substances also exhibit a risk, insofar as they have, at a fairly low concentration, a potent pharmacodynamic activity: antibiotics, anticancer agents, steroidal anti-inflammatories, immunodepressants, hormones.

The risks are very high when the receptacle containing these substances is broken inside the lyophilizer container as a result of a faulty resistance which is always possible or during the automatic stoppering.

On the other hand, upon discharging the lyophilizer container, there is a risk of introducing bacteria, yeasts, fungi coming from the surrounding atmosphere.

The use of sterilizing gas such as formaldehyde or ethylene oxide poses delicate problems of dosage and distribution inside the container of a lyophilizer.

The germs sterilized by these means (steam, ethylene oxide, formaldehyde) are no longer capable of multiplying, but their possible residues may present a toxicity risk: such is the case during the destruction of Gram-negative bacteria which release, in this case, soluble lipopolysaccharides, bringing about pyrogenic reactions in injectable products.

SUMMARY OF THE INVENTION

By virtue of the present invention, the Applicant proposes reducing these risks, either by a new means for decontaminating "in situ" free harmful products or those released in the lyophilizer container during the freeze-drying process itself, or by a new means for sterilizing the container.

Within the scope of the present description, the term "decontamination" will be used to designate the use of a product with biocidal, depyrogenating or neutralizing activity in general.

The present invention therefore relates to a method for decontaminating or sterilizing a vacuum sealed container in which microorganisms, which may be pathogenic, or dangerous substances, especially pyrogenic substances or substances having a harmful influence on the environment are present, characterized in that a gas or a liquid capable of vaporizing under the conditions prevailing in the container, and exhibiting biocidal properties towards the said microorganism which may be pathogenic and/or neutralizing properties towards the said dangerous substances, is introduced into the container.

According to one variant of the invention, the method is characterized in that one or more containers, closed or alternatively open, containing microorganisms which may be pathogenic and/or dangerous substances are present inside the sealed container and in that the said gas or the said liquid are introduced before opening the sealed container in order to remove a receptacle or the receptacles.

According to another variant of the invention, the lyophilizer container may be sterilized before loading, by injecting ozone, for example in order to ensure its sterility between two operations.

According to one of the characteristics of the invention, the microorganism which may be pathogenic and/or the dangerous product is dehydrated, in particular by lyophilization, spray-drying or vacuum-drying.

The decontamination treatment occurs preferably after the lyophilization cycle which the product undergoes. Indeed, this method makes it possible to take advantage of the vacuum created inside the container and of the possibility of cooling or heating the products contained in the container. The temperature of the decontaminating mixtures may range between −50° C. and +150° C. When the normal lyophilization cycle for a hazardous product is completed, the receptacles of dry product are automatically stoppered inside the tank. The container is again placed under vacuum, if the stoppering was carried out under an inert atmosphere, this in order to avoid leaks to the outside and the cooling system may be kept in operation, so as to create condensation surfaces. The existence of this vacuum easily permits decontamination in this case by vaporization of a liquid or introduction of a gas, the cooling of the container permits condensation on the cold surfaces to be decontaminated.

The liquid intended to be vaporized must of course be adapted to the microorganism, which may be pathogenic, to be destroyed or to the toxic to be neutralized. It may be aqueous or organic solutions.

Among the solutions or gases which can be used, those exhibiting biocidal, especially bactericidal and/or virucidal, properties and oxidizing compositions should be mentioned.

In particular, aqueous solutions of peracetic acid, hydrogen peroxide or alcohol or mixtures, especially of peracetic acid and H2O2 or of alcohol and H2O2 may be used.

Among the mixtures using organic solutions, there should be mentioned:

mixtures of hydrophilic/lipophilic solvents such as methanol/chloroform or mixtures of lipophilic solvents (for example diethyl ether) made inert by means of nitrogen, $CO_2$ or freons or freon substitutes.

The injection of a previously generated gas also forms part of the invention insofar as this gas has especially oxidizing or virucidal properties. Among these gases, there should be mentioned:

gaseous mixtures consisting of oxygen and ozone or of oxygen, ozone and carbon dioxide or gaseous mixtures in a volatile solvent, for example oxygen/ozone in solution in a freon (F22, F11, F113) or freon substitutes.

The injection of the liquid phases is performed through an injector disperser which causes the atomization of the mixture in aerosol form in the container.

The pressure inside the container is kept at a sufficiently low value in order:

1/ to remain under vacuum relative to the external atmospheric pressure, in order to avoid leaks of inactivating agent.

2/ to preserve a vapor pressure sufficient to obtain a gaseous phase for the solvent/s injected.

The treatment preferably lasts for 30 minutes to 10 hours, according to the nature of the desired decontamination.

During the treatment period, the thermal modulation of the container is adjusted according to the desired effect; the negative temperatures and the positive temperatures are adjusted as a function of the stability of the product to be decontaminated.

The method of decontamination according to the invention applies to potentially dangerous biological products which may present a hazard for the environment if they are not confined in a hermetic and sealed manner in a receptacle: viruses, bacteria (sporulating or otherwise), fungi, yeasts, nucleic acids.

In the case where the gas is ozone, the sterilization, decontamination and depyrogenation method is performed under defined temperature and pressure conditions to which the ozone is subjected.

The ozone is continuously generated from atmospheric oxygen, but for reasons to do with quality and conformity, the source of gas is pure oxygen, which is introduced into a high-voltage generator. The regulation of the oxygen flow rate and the applied electrical voltage determine the ozone concentration of the emerging gas.

Thus, the ozone is not used in the form of pure gas, but generated from oxygen, preferably air, by means of a generator delivering known concentrations of ozone in oxygen which may for example be in a range between 4 µg/ml and 110 µg/ml (4 mg/l to 110 mg/l). The mode of ozone generation from oxygen forms part of the technical knowledge of persons skilled in the art: for example high-voltage, ultraviolet radiation, electrochemical cell generator.

The principle according to the invention therefore consists in injecting, through a valve into the container of a lyophilizer, an oxygen/ozone mixture. The container is previously placed under vacuum (1 Pa to 0.1 Pa equivalent to $10^{-2}$ to $10^{-3}$ mbar). The gas flow rate is provided by the pressure applied at the outlet of the generator.

This gas flow rate may also be regulated by the gas injecting device fitted on the lyophilizer, which permits a constant controlled addition of fresh gas.

The container may be loaded with lyophilized products and the decontamination-sterilization may occur at the end of the lyophilization cycle.

The ozone/oxygen mixture is then injected at the desired concentration (4 µg/l to 110 mg/l) until a pressure less than or equal to 0.8 bar (equivalent to $8 \times 10^6$ Pa) is obtained inside the container.

The temperature of the shelves may be adjusted between $-20°$ C. and $30°$ C.

The residence time of the ozone/oxygen mixture is between 4 minutes and 3 hours.

The mode of ozone sterilization may be improved in certain cases of sporulating bacteria by humidifying the gas between 10% and 95% of water vapor.

Similarly, the pH of the humidified mixture may be adjusted by addition of carbon dioxide so as to destroy more rapidly acid-sensitive germs.

In the case of a sterilization cycle, that is to say before introducing the pathogenic agents or the dangerous substances to be treated, the procedure may be carried out in the following manner:

Into the container placed under vacuum (1 Pa to 0.1 Pa, equivalent to $10^{-2}$ to $10^{-3}$ mbar), an oxygen/ozone mixture, containing 30 to 70 mg of ozone per liter of mixture, is injected until the pressure in the container rises to 0.8 bar ($8 \times 10^6$ Pa).

The temperature of the shelves is adjusted to $+10°$ C. ($\pm 20°$ C.).

The mixture is kept in contact with the container for one hour ($\pm 30$ min).

The container is then again placed under vacuum by means of a pump. The gas evacuation route comprises a means for destroying the residual ozone, such as for example an activated carbon filter.

A second injection of the oxygen/ozone mixture may then be performed under similar conditions in order to homogenize the distribution of the gas, in the case of a container with a complex geometry.

The contact time is maintained for 30 minutes.

It is possible, according to another embodiment of the invention, to regulate the injection of ozone by means of the gas injecting device specific to the lyophilizer so as to maintain a constant partial pressure of ozone.

The oxygen/ozone mixture is then repumped and neutralized.

The chamber, again placed under vacuum, may be flushed with a sterile inert gas (for example nitrogen) in order to remove the residual ozone.

In the case of a decontamination/depyrogenation cycle after the products have been subjected to drying, the procedure may be carried out in the following manner:

Into the container placed under vacuum (1 Pa to 0.1 Pa, equivalent to $10^{-2}$ to $10^{-3}$ mbar), an oxygen/ozone mixture, containing 50 to 100 mg of ozone per liter of mixture, is injected until the pressure in the container rises to 0.8 bar ($8 \times 10^6$ Pa).

The temperature of the shelves is adjusted to $+10°$ C. ($\pm 20°$ C.). The contact time of the gaseous mixture with the contaminants coming from the lyophilization aerosols or with the pyrogenic substances generated is between 30 minutes and 3 hours. When the contaminant is likely to contain a carbon-carbon double bond, it may be useful to accelerate the hydrolysis of the ozonide formed by injecting a humidified gas, containing 10 to 95% relative humidity.

At the end of the cycle, the gaseous mixture is aspirated by means of a pump through a device for removing the residual ozone.

This device consists of a cartridge containing activated carbon. Other means for removing ozone are known in the state of the art: UV rays, potassium iodide, thermolyzes and the like.

The container may in this case be flushed with an inert gas (for example nitrogen) in order to remove the traces of residual ozone.

The invention also applies to pharmacologically active products for human or veterinary medicine, especially when it is known that the product to be treated is sensitive to oxidation.

This is the case for certain categories of medicinal products:

Antibiotics:
- Oligomycin, containing a C=C double bond and a diene.
- Penicillin, containing an aromatic ring, or a double bond or a sulfur atom in the molecule.

Immunodepressants:
- Clyclosporin, containing a double bond.

Anticancer agents:
- Melphalan, containing an aromatic ring.

Corticoids:
- Dexamethasone, containing a double bond.

Hormone: GHRH.

Chelating agents:
- Dimercaptol.

Prostaglandins.

All these substances are capable of reacting with ozone, and then possibly with peracetic or performic acid, to give pharmacologically inactive derivatives.

The invention also applies to the removal of undesirable compounds which may accidentally occur in active products such as for example formalin or endotoxins.

The invention also relates to a device for implementing the method as it has just been described above.

This device for injecting and controlling decontaminating mixtures which permit the implementation of the method consists of a container in which are housed one or more supports for the products to be decontaminated, one or more means of cooling and heating and a means of placing under vacuum, characterized in that the said container is equipped with one or more means of supplying gas or liquid according to the preceding description and one or more means of evacuating the said gases or liquids.

Preferably, the device comprises one or more means of supplying a flush gas which makes it possible to accelerate the evacuation of the said gases or liquids. The device also comprises a system for regulating the injection of gas in order to admit controlled quantities of gas.

BRIEF DESCRIPTION OF THE DRAWING

The FIGURE is a schematic cutaway view of a specific device which makes it possible to implement the method according to the invention.

DETAILED DESCRIPTION OF THE INVENTION

The device 1 consists of a container 2, in which is housed a condenser 5 surmounted at an appropriate distance by a heating support 4 intended to receive the receptacles. A pressure gauge 3 is attached to the upper wall 13 of the container. The said container is equipped, on a side wall 14, with an inlet 6 connected via a tube 12 to an ozone generator (not shown) and with an inlet 7 for an inert gas. The lower wall 15 is equipped with an outlet 8 connected via a tube 16 to a vacuum pump 11 and with another outlet 9 connected via a drain 17 to a vacuum pump 11, a trap 10 containing activated carbon being mounted in series between the inlet 9 and the pump 11. The abovementioned tubes or drains are equipped with stop valves 18.

The advantages and possible applications of the present invention will appear more clearly in the following examples, given by way of illustration of the invention, without limiting its field of application.

EXAMPLE I

A suspension of virus of the microviridiae $\phi \times 174$ bacteriophage family is frozen and lyophilized. The suspension initially contains $10^7$ infectious particles per ml, expressed in PFU/ml.

The titration system is performed by means of a uniform colony of *E. coli* growing on agar.

By 10-fold serial dilutions of the viral suspension, the original titer is obtained when the number of lysis plaques appearing after incubating the inoculated agar for 18 h at 37° C. is between 30 and 300.

After lyophilization, 500 ml of 70% ethyl alcohol are injected into the container and left in contact for 30 minutes.

The lyophilizer plates are adjusted to $-40°$ C.

Results:

lyophilized control stoppered under vacuum: $10^6$ PFU/ml open bottle in contact with 70% alcohol: $2.1 \times 10^2$ PFU/ml Equivalent to a reduction of 3.7 Log

EXAMPLE II

Under the same conditions as in Example I, hydrogen peroxide at 30 volumes is injected in an amount of 500 ml. It is maintained in contact for 10 minutes.

The control viral suspension, stoppered under vacuum, contained after lyophilization $10^5$ PFU/ml.

The open bottle, in contact with hydrogen peroxide, now has only 30 PFU/ml.

The reduction in viral titer obtained is 4.5 Log.

EXAMPLE III

Under the same conditions as in Example I, there are injected successively after lyophilization, first 500 ml of hydrogen peroxide at 30 volumes; it is left in contact for 10 minutes; then 500 ml of 70% ethyl alcohol are injected and left in contact for 30 minutes.

In this example, the lyophilization was deliberately poorly performed so as to leave a high residual humidity (>20%) in the treated product.

In this case, the reduction in viral titer obtained by the treatment is only 1.1 Log (control stoppered under vacuum= $4 \times 10^5$ PFU/ml; bottle in contact with inactivating agents= $3 \times 10^4$ PFU/ml).

This example demonstrates that the product to be treated must be dried beforehand in order to absorb the inactivating agent in place of water.

EXAMPLE IV

Under the same conditions as in Example 1, 500 ml of hydrogen peroxide at 30 volumes and 500 ml of 70% ethyl alcohol are injected successively. The lyophilized control bottle contains 5×10³ PFU/ml.

The bottle in contact with the inactivating agents no longer contains a detectable infectious particle. The reduction in viral titer obtained is ≧3.7 Log.

EXAMPLE V

A suspension of ⌀×174 bacteriophage virus is lyophilized in its preservation medium as in Example 1.

After the drying cycle, a 10% (vol/vol) solution of peracetic acid is injected into the lyophilizer tank.

The control bottle stoppered under vacuum contains 1.85×10⁴ PFU/ml.

The bottle in contact with the inactivating agent contains no detectable infectious particle.

The reduction in viral titer is ≧4.3 Log.

EXAMPLE VI

With the objective of applying the inactivation method to a potentially infectious product, a suspension of ⌀×176 bacteriophage virus is mixed with a solution of immunoglobulins extracted from human plasma: 100 ml of human immunoglobulin solution contains 20 ml of suspension of ⌀×174 at 1.52×10⁷ PFU/ml.

After lyophilization of the product, 500 ml of hydrogen hydroxide [sic] at 30 volumes, then after 10 minutes of contact, 500 ml of 70% ethyl alcohol are successively injected into the lyophilizer tank.

The level of reduction observed is 1.52 Log.

EXAMPLE VII

A solution of immunoglobulins extracted from human plasma is supplemented with ⌀×174 bacteriophage virus as in Example VI: 100 ml of immunoglobulin solution contains 20 ml of ⌀×174 at 3.7×10⁸ PFU/ml.

The final solution still contains 4.5×10⁴ PFU/ml; the reduction in viral titer is attributable to the presence of specific antibodies in the immunoglobulin preparation used.

After lyophilization, a mixture consisting of 100% absolute alcohol diluted with hydrogen peroxide at 10 volumes such that the final alcoholic titer is 70%, is injected into the lyophilizer tank.

The bottle in contact with the inactivating agent contains no detectable infectious particle.

The reduction in viral titer is ≧4.65 Log.

EXAMPLE VIII 50 ml of injectable albumin solution extracted from human plasma and containing 50 g/l of albumin is supplemented with 10 ml of a suspension of ⌀×174 bacteriophage virus with a titer of 6.55×10⁸ PFU/ml.

After lyophilization of the solution, a gaseous mixture containing oxygen and ozone is injected into the container. The ozone is obtained by means of high-voltage electric discharge in a stream of pure oxygen; the quantity generated is 40 μg/ml of ozone. The injection is carried out until a pressure of −0.2 bar is obtained in the container. The mixture is kept in the lyophilizer for 30 minutes.

The gas is then aspirated through a neutralizing agent consisting of a solution of potassium iodide.

The tank is then again placed under atmospheric pressure. No bottle treated in the lyophilizer contains detectable infectious particles.

The reduction in viral titer obtained is ≧8.8 Log.

EXAMPLE IX

A solution of immunoglobulins extracted from human plasma proved to be non-conforming during the trials recommended by the Pharmacopeia, especially with respect to the measurement of the pyrogenic effect on rabbits.

This lyophilized non-conforming product is placed in the lyophilizer container and placed under vacuum.

The ethylene alcohol [sic]/hydrogen peroxide mixture as described in Example VII is then injected.

After a contact time of 30 minutes, the tank is purged and the treated bottles are stoppered under vacuum.

The trial of pyrogenic substances on rabbits shows a rise in temperature of 1°45 for 3 rabbits upon injection of the untreated product.

Injection of the product treated according to the modalities of Example X cause only a minimal rise in temperature of 0.7° C. for 3 rabbits.

The treated product thus conforms to the requirements relating to the trial of pyrogenic substances.

EXAMPLE X

A solution of the coagulation factor FVIII extracted from human plasma was accidentally contaminated with endotoxins of bacterial origin. The lyophilized bottles are placed in the lyophilizer tank and evacuated under vacuum.

A gaseous mixture of oxygen and ozone obtained according to the same method as in Example VIII is then injected.

The mixture is kept in contact with the product for 30 minutes.

After again placing under atmospheric pressure, the bottles are titrated for their endoxotin content using a specific test (Limulus Amebocyte Lysate: LAL). The concentrations are expressed in Endotoxin Units/ml (EU/ml) relative to a reference endotoxin.

The untreated bottle contains 327 EU/ml; the product treated according to Example X contains 116 EU/ml, equivalent to a reduction of 64.5% in the endotoxin level.

EXAMPLE XI

A suspension, in nutrient broth, of *E. coli* containing 10⁶ *E. coli* germs per ml is dried on a strip of filter paper.

The strip is then reimmersed in a nutrient broth in order to initiate the culture of *E. coli*.

Serial dilutions in 9% NaCl (or 9 g/l) are inoculated on tryptone-soya agar plates in order to enumerate the residual germs.

The strips are then placed in a lyophilizer.

The ozone sterilization is carried out according to the method described: 50 μg/ml 03 [sic], T°=10° C., 30 min of contact.

After reculturing the strip treated according to this method, no *E. coli* bacteria is detected after 7 days of contact with the nutrient medium at 37° C.

The strip trial is repeated with a culture of *Bacillus subtilis*, in a manner similar to the preceding trial.

Under the ozone sterilization conditions: 50 μg/ml, T°=10° C. and 60 min of contact, no bacillus growth is detected after 7 days of contact between the treated strip and the nutrient medium.

We claim:

1. A process for decontaminating or sterilizing at least one vacuum sealed container containing (a) biological material having the ability to replicate or (b) containing a pyrogenic substance, said process comprising the steps of dehydrating under vacuum said biological material having the ability to replicate or said pyrogenic substance, and introducing, after dehydration, while maintaining a vacuum (c) an aqueous solution selected from the group consisting of aqueous solutions of peracetic acid, hydrogen peroxide, a mixture of peracetic acid and hydrogen peroxide, and a mixture of alcohol and hydrogen peroxide, or (d) an aqueous gas capable of vaporizing under vacuum selected from the group consisting of (i) a gas which is a mixture of oxygen and humidified ozone and (ii) a gas which is a mixture of carbon dioxide, oxygen and humidified ozone into the container such that the (c) aqueous solution or (d) aqueous gas is kept in contact with the (a) dehydrated biological material or (b) dehydrated pyrogenic substance, such that condensation of the aqueous solution or aqueous gas occurs on the material.

2. The process as claimed in claim 1, wherein the container contains (a) biological material, which is a pathogenic microorganism.

3. The process as claimed in claim 1, wherein the dehydration is accomplished by lyophilization, spray-drying, or vacuum-drying.

4. The process as claimed in claim 1, wherein the (c) aqueous solution is introduced into the container under vacuum, wherein the aqueous solution is peracetic acid in distilled water.

5. The process as claimed in claim 1, wherein the (d) aqueous gas is introduced into the container under vacuum, wherein the aqueous gas is a mixture of oxygen and humidified ozone.

6. The process as claimed in claim 1, wherein the introduction of the (c) aqueous solution or the (d) aqueous gas under vacuum into the container is accomplished by means of an injector or a disperser.

7. The process as claimed in claim 1, wherein the container is a lyophilization container.

8. The process as claimed in claim 1, wherein the (c) aqueous solution or (d) aqueous gas is kept in contact with the (a) dehydrated biological material or (b) dehydrated pyrogenic substance for a period of from 30 minutes to 10 hours.

9. The process as claimed in claim 1, wherein the (c) aqueous solution or (d) aqueous gas is heated to a temperature of between $-50°$ C. and $+150°$ C. after being introduced into the container.

10. The process as claimed in claim 1, wherein the (c) aqueous solution is introduced into the container, wherein the aqueous solution is a mixture of peracetic acid and hydrogen peroxide or a mixture of alcohol and hydrogen peroxide.

11. The process as claimed in claim 10, wherein the aqueous solution is a mixture of alcohol and hydrogen peroxide and the alcohol is ethanol.

12. The process as claimed in claim 1, wherein the aqueous gas is introduced into the container, and wherein the aqueous gas is carried in a volatile solvent.

13. A process for decontaminating or sterilizing at least one vacuum sealed container containing (a) biological material having the ability to replicate or (b) containing a pyrogenic substance, said process comprising the steps of dehydrating under vacuum said biological material having the ability to replicate or said pyrogenic substance, and introducing, after dehydration, under vacuum (c) an aqueous solution selected from the group consisting of aqueous solutions of peracetic acid, hydrogen peroxide, alcohol, and mixtures thereof, or (d) an aqueous gas capable of vaporizing under vacuum selected from the group consisting of (i) a gas which is a mixture of oxygen and humidified ozone and (ii) a gas which is a mixture of carbon dioxide, oxygen and humidified ozone into the container such that the (c) aqueous solution or (d) aqueous gas is kept in contact with the (a) dehydrated biological material or (b) dehydrated pyrogenic substance, such that condensation of the aqueous solution or aqueous gas occurs on the material.

* * * * *